(12) United States Patent
Karlsson et al.

(10) Patent No.: US 9,782,372 B2
(45) Date of Patent: *Oct. 10, 2017

(54) PHARMACEUTICAL COMPOSITION FOR THE TREATMENT OF FUNGAL INFECTIONS

(71) Applicant: MOBERG PHARMA AB, Bromma (SE)

(72) Inventors: Ewa Karlsson, Bromma (SE); Sahar Feizollahi Ashkar, Bromma (SE); Peter Kaufmann, Bromma (SE)

(73) Assignee: Moberg Pharma AB, Bromma (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/609,142

(22) Filed: Jan. 29, 2015

(65) Prior Publication Data

US 2015/0306052 A1  Oct. 29, 2015

Related U.S. Application Data

(63) Continuation of application No. 14/193,304, filed on Feb. 28, 2014, now Pat. No. 8,987,330.

(30) Foreign Application Priority Data

Mar. 15, 2013 (WO) ................ PCT/GB2013/050654

(51) Int. Cl.
| | | |
|---|---|---|
| *A61K 31/17* | (2006.01) | |
| *A61K 31/19* | (2006.01) | |
| *A61K 31/047* | (2006.01) | |
| *A61K 9/00* | (2006.01) | |
| *A61K 47/10* | (2017.01) | |
| *A61K 9/08* | (2006.01) | |
| *A61K 31/197* | (2006.01) | |

(52) U.S. Cl.
CPC ............ *A61K 31/19* (2013.01); *A61K 9/0014* (2013.01); *A61K 9/08* (2013.01); *A61K 31/047* (2013.01); *A61K 31/17* (2013.01); *A61K 31/197* (2013.01); *A61K 47/10* (2013.01)

(58) Field of Classification Search
CPC ....... A61K 31/19; A61K 31/047; A61K 31/17
USPC .................................................. 514/557, 588
See application file for complete search history.

(56) References Cited

U.S. PATENT DOCUMENTS

| | | |
|---|---|---|
| 4,296,130 A | 10/1981 | Herschler |
| 4,672,078 A | 6/1987 | Sakai et al. |
| 5,525,635 A | 6/1996 | Moberg |
| 5,696,164 A | 12/1997 | Sun et al. |
| 6,573,301 B1 | 6/2003 | Glassman et al. |
| 8,158,138 B1 | 4/2012 | Landau et al. |
| 8,987,330 B2 | 3/2015 | Karlsson et al. |
| 2007/0098654 A1 | 5/2007 | Patel et al. |

FOREIGN PATENT DOCUMENTS

| | | |
|---|---|---|
| EP | 292495 B1 | 9/1991 |
| JP | 2001019610 A | 1/2001 |
| WO | WO-87/04617 A1 | 8/1987 |
| WO | WO-03/080051 A1 | 10/2003 |
| WO | WO-03/090736 A1 | 11/2003 |
| WO | WO-2012/110430 A1 | 8/2012 |

OTHER PUBLICATIONS

Emtestam, et al., "Treatment of distal subungual onychomycosis with a topical preparation of urea, propylene glycol and lactic acid: results of a 24-week, double-blind, placebo-controlled study", *Mycoses*, 2012, 55:532-540.

Faergemann, et al., "Early and Visible Improvements after Application of K101 in the Appearance of Nails Discoloured and Deformed by Onychomycosis", *Journal of Cosmetics, Dermatological Sciences and Applications*, 2011 1:59-63.

Gentinor®, product package and package insert, Mar. 2011.

Brown, et al.; "The Stability of Solutions of Urea Peroxide in Glycerol, Isopropanol, and Ethylene Glycol"; Journal of the American Pharmaceutical Association; 35(10):304-305 (Oct. 1946).

Fluhr et al.; "Glycerol—Just a Moisturizer? Biological and Biophysical Effects"; Dry Skin and Moisturizers: Chemistry and Function; Edited by: Loden et al., CRC Press; Chapter 20, pp. 227-243 (Nov. 9, 2005)[ISBN: 978-0-8493-2134-4].

*Primary Examiner* — Kevin E Weddington
(74) *Attorney, Agent, or Firm* — McCarter & English, LLP; Steven G. Davis; Xin Zhang

(57) ABSTRACT

There is provided pharmaceutical compositions suitable for topical application to the nail for the treatment of nail diseases such as onychomycosis, comprising a urea-based component, a diol component, such as propylene glycol, an organic acid component, such as lactic acid, and a triol component, such a glycerol. There is further provided methods of improving the storage stability of a pharmaceutical composition suitable for topical application to the skin and/or nails comprising such urea-based components, diol components, organic acid components, and, optionally, an aqueous base, which method comprises adding a triol component, such a glycerol, to that composition prior to said storage.

36 Claims, 1 Drawing Sheet

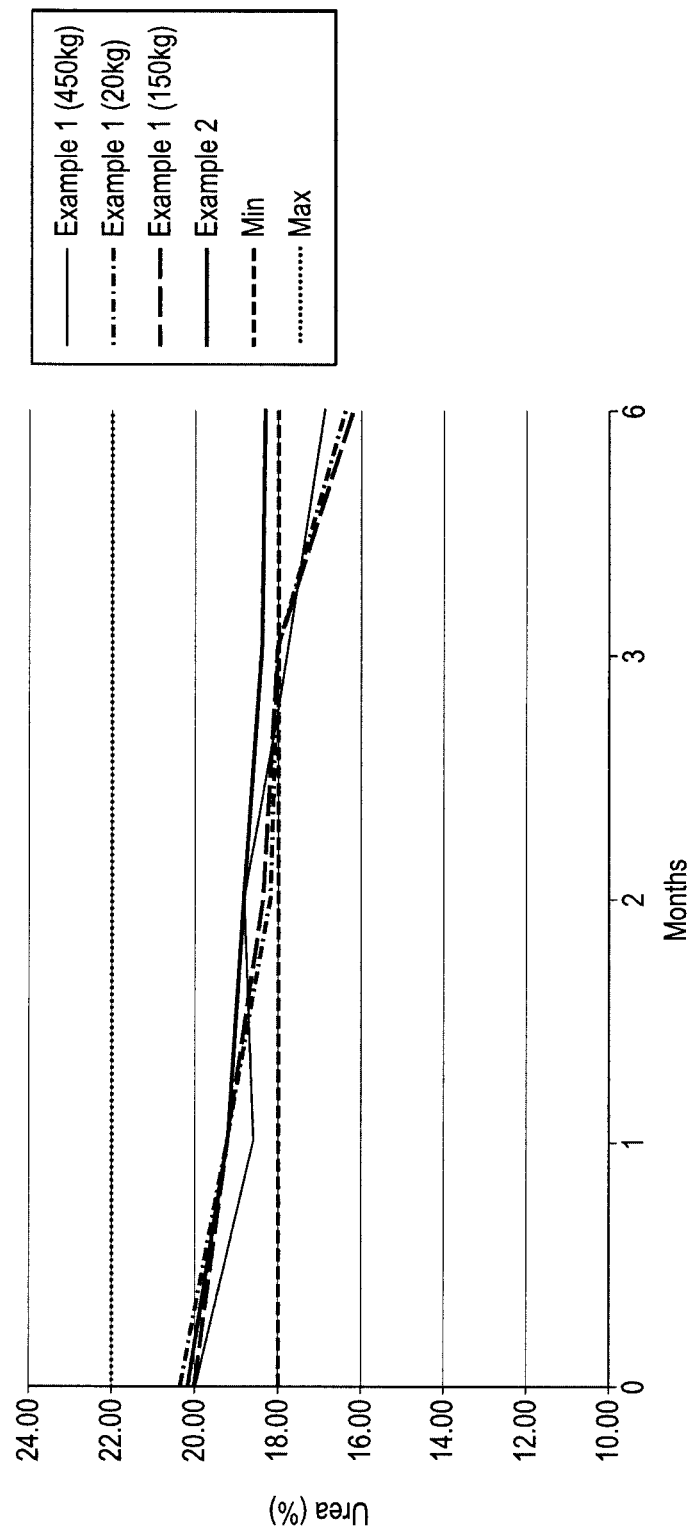

PHARMACEUTICAL COMPOSITION FOR THE TREATMENT OF FUNGAL INFECTIONS

RELATED APPLICATIONS

This application is a continuation of allowed U.S. patent application Ser. No. 14/193,304, filed on Feb. 28, 2014, which claims the benefit of International Application No.: PCT/GB2013/050654, filed on Mar. 15, 2013, the entire teachings of which are incorporated herein by reference.

BACKGROUND

This invention relates to new pharmaceutical compositions that are useful in topical application for the treatment of fungal nail infections, in particular onychomycosis.

Fungal infections of the nail are much more prevalent than is commonly perceived. It is often understood to be a niche problem, affecting only a few people. In fact, it is the most common disease of the nail, affecting about 100 million patients in Europe and North America. Prevalence is about 10% in the general population and over 25% in the over-50s.

Onychomycosis is the most common fungal disease of the nail and affects about 6 to 8% of the adult population. Onychomycosis can affect both toenails and fingernails and is chiefly manifest by thickening and discoloration of the nails. This results in the formation of opaque, thick and/or friable nail lesions caused by the invasion of fungi. The nail becomes dry, and breaks or flakes, often exhibiting a yellowish colour.

Nails that become hard and thick, make the care of the nail more difficult. Infected toenails can grow so thick that shoes became uncomfortable to wear. In extreme cases, destruction of the nail may result. Additionally, a perceived unsightliness in infected nails can lead to confidence and/or self esteem problems in situations when the hands and/or feet are necessarily exposed.

In addition to onychomycosis, about 40% of all patients with psoriasis are affected by changes in the nail. Dryness and/or superficial damage can also result in unsightly and discolored nails.

Nail fungus is also a very difficult condition to treat. Treatment times are often long; it can take a year or more for an infected nail to come away and a healthy new nail to grow out. Such longevity of treatment is known to cause poor compliance, meaning that the majority of patients are poorly treated or, in essence, untreated.

Significant effort has been directed towards research into alternative and/or better treatments of fungal infections of keratinous structures such as the nail.

Much of the research effort has been directed towards pharmaceutical formulations that attempt to administer a recognized antifungal compound, such as imidazoles, triazoles, thiazoles, echinocandins and allylamines (hereafter "antifungal drug compounds") into the nail structure. However, the problem of obtaining distribution of sufficient concentrations of such antifungal drug compounds throughout the nail and into the nail bed has proven to be a difficult one to solve. Thus far, a completely satisfactory solution eludes practitioners. Promising laboratory results for new formulations comprising antifungal drug compounds have often been followed by disappointing result in the clinic.

An efficacious pharmaceutical formulation that does not comprise an antifungal drug compound as such (including any of those listed above or hereinafter) is disclosed in international patent application WO 87/04617, U.S. Pat. No. 5,525,635 and European Patent No. EP 292 495 B1. Here, a composition for the treatment of inter alia mycosis of the skin and nails is disclosed that comprises, as its main active components, propylene glycol and urea, although lactic acid may also be included.

The efficacy and safety of this formulation have been documented in several clinical trials (see, for example, Emtestam, Kaaman and Rensfeldt (2012), *Mycoses*, 55, 532 (2012) and Faergemann, Gullstrand and Rensfeldt, *Journal of Cosmetics, Dermatological Sciences and Applications*, 1, (2011)). Furthermore, a product based on this formulation is sold under the trademark Emtrix®, or Nalox®. It is indicated primarily in the treatment of nail discoloration and damage caused by fungal nail infection or psoriasis.

Emtrix® ingredients are all GRAS (General Regarded as Safe by FDA) listed compounds and are fully biodegradable. The product is free from preservatives and fragrances. It is applied as a solution directly to the damaged nail.

Despite the efficacy of this product, we have found that the chemical stability of the solution could be improved at higher storage temperatures. In particular, the urea in such formulations chemically degrades. This instability is unexpectedly solved by the addition of a triol, such as glycerol, to the liquid formulation.

Glycerol is commonly used as a constituent in cosmetic and pharmaceutical formulations. See, for example, international patent application WO 03/090736 and U.S. Pat. No. 8,158,138.

The use of urea hydrogen peroxide (or carbamide peroxide) as a whitening agent is known from U.S. Pat. No. 6,573,301 and US Patent Application No. 2007/0098654. In Japanese patent application No. 2001-019610, a composition for skin (topical) application comprising urea is stabilised by the addition of a nucleotide in combination with an ester derived from a short fatty acid and glycerol.

International patent application WO 2012/110430 describes pharmaceutical compositions comprising solvents, in which urea is rendered in the solid state prior to application of the composition to e.g. the nail of a subject and evaporation of an organic solvent. Glycerol is mentioned as an agent that may be included to improve the "washability" of the composition after the organic solvent has evaporated.

SUMMARY

To the applicant's knowledge, there is no disclosure in the prior art of the use of a triol, such as glycerol, to stabilise chemically urea when the latter is dissolved or presented in a liquid- or solution-based pharmaceutical composition.

According to a first aspect of the invention there is provided a pharmaceutical composition suitable for topical application to the skin and/or, preferably, the nails, which composition comprises:

(a) for example about 1% to about 35% by weight based upon the total weight of the composition of a urea-based component;

(b) for example about 40% to about 80% by weight based upon the total weight of the composition of a diol component;

(c) for example about 1% to about 20% by weight based upon the total weight of the composition of an organic acid component; and (d) for example about 4.5% to about 12% by weight based upon the total weight of the composition of a triol component; and (e) optionally aqueous base.

Such compositions are referred to hereinafter as "the compositions of the invention".

DETAILED DESCRIPTION OF THE FIGURE

FIG. 1 shows a comparison of chemical stability of compositions of the invention compared to a commercial composition of the prior art

DETAILED DESCRIPTION OF THE INVENTION

Aqueous base may be included in compositions of the invention due to the presence of an organic acid component. In this respect, the pH of the final formulation may need to be raised to comply with e.g. regulatory requirements by the addition of a small amount of aqueous base (such as aqueous sodium hydroxide, e.g. 10M NaOH (aq.)). Final pHs of formulations are preferably in the range of about 2 to about 6 (e.g. about 3.5 to about 5, e.g. to about 4.5). Up to about 30% of water may in any event be included in compositions of the invention.

Wherever the word "about" is employed herein in the context of amounts (e.g. relative amounts, such as percentage amounts, of individual constituents in a composition or a component of a composition and absolute doses (including ratios) of active ingredients and/or excipients), temperatures, pressures, times, pH values, pKa values concentrations, etc., it will be appreciated that such variables are approximate and as such may vary by ±10%, for example ±5% and preferably ±2% (e.g. ±1%) from the numbers specified herein.

The urea-based component may comprise urea itself, and/or may comprise urea peroxide, also known as urea hydrogen peroxide (UHP), percarbamide or carbamide peroxide, which is an adduct of hydrogen peroxide and urea, and is used mainly as a disinfecting or bleaching agent in cosmetics and pharmaceuticals. We have found that the addition of urea peroxide improves the visual appearance of the nail more rapidly when such compositions of the invention are employed. This in turn leads to improved compliance; an improvement in appearance provides an incentive for the patient to continue treatment.

The diol component comprises at least one diol. Non-limiting examples of the diol component are ethylene glycol, propylene glycol, butanediol, pentanediol (for example 1,5-pentanediol), hexanediol, and mixtures thereof. If desired, the diol component may be a mixture of diols such as a mixture of propylene glycol and another diol, such as 1,5-pentanediol. A preferred diol is propylene glycol.

Organic acidic components that may be employed enable the provision (at the site of application of compositions of the invention) of a pH of between about 2.0 (e.g. about 3.5) and about 6.5. For the purpose of this invention, the term includes substances that are safe for use in mammals, such as weak acids. Typical pKas of weak acids are in the range of between about −1.5 (e.g. about −1.74, such as about 1.00, e.g. 2.00 and about 16 (e.g. about 15.74) (e.g. see Vollhardt, *Organic Chemistry* (1987)). A preferred range is between about 1 and about 10.

The organic acid component may thus comprise a $C_{1-10}$ carboxylic acid, which may be provided pure/neat and/or in (e.g. aqueous) solution. Examples of $C_{1-10}$ carboxylic acid include saturated and/or unsaturated, straight and/or branched aliphatic mono-, di- and polycarboxylic acids having 1, 2, 3, 4, 5, 6, 7, 8, 9 or 10 carbon atoms, alkylaryl or aromatic dicarboxylic acids, oxy and hydroxyl carboxylic acids (e.g. alpha-hydroxy acids) having 1, 2, 3, 4, 5, 6, 7 or 8 carbon atoms. Examples of suitable organic acid components include one or more of formic acid, acetic acid, propionic acid, butyric acid, valeric acid, caproic acid, capryic acid, capric acid, sorbic acid, oxalic acid, hydroxybutyric acid, hydroxypropionic acid (e.g. 2-hydroxypropionic acid, hereinafter lactic acid), glycolic acid, citric acid, malic acid, tartaric acid, malonic acid, fumaric acid, succinic acid, glutaric acid, apidic acid, pimelic acid, oxalacetic acid, phthalic acid, tartronic acid and pyruvic acid. Preferred organic acids include hydroxy acids, such as hydroxybutyric acid, hydroxypropionic acids (e.g. lactic acid), glycolic acid, citric acid, malic acid and tartaric acid. More preferred organic acids include lactic acid. Lactic acid may be provided in e.g. a 90% aqueous solution.

Urea-based components, diol components and/or organic acid components may be employed in pharmacologically effective amounts, which refers to amounts of such components that are capable, in combination, of conferring a desired therapeutic effect on a treated patient, whether administered alone or in combination with another ingredient. Such an effect may be objective (i.e. measurable by some test or marker) or subjective (i.e. the subject gives an indication of a positive effect).

Individual amounts of urea-based, diol and organic acid components that may be employed in combination in compositions of the invention may be determined by the skilled person, in relation to what will be most suitable for an individual patient. Although this may vary with the type and severity of the condition that is to be treated, and the response of the particular patient to be treated, typical total amounts that may be employed in a composition of the invention of:
  (i) urea-based components are in the range of about 1% to about 35%, such as about 3% (e.g. about 5%) to about 30%, for example about 8% (e.g. about 10%) to about 25%; and
  (ii) diol components are in the range of about 40% to about 80%, such as about 45% to about 75%, for example about 50% to about 70%; and
  (iii) organic acid components are in the range of about 1% (e.g. about 2%) to about 20%, preferably from about 3% (e.g. about 4%) to about 15%, and more preferably from about 5% (e.g. about 8%) to about 12%,
by weight based upon the total weight of the composition.

Suitable concentration ratios of the organic acid component and the diol component from about 1:20 to about 1:1, preferably from about 1:15 to about 1:2 and more preferably from about 1:12 to about 1:4, by weight based on the total weight of the composition.

The total combined concentration of the diol component and the organic acid component in the formulation are preferably in the range of about 50% to about 90%, such as about 55% to about 85%, for example about 60% to about 80%.

Compositions of the invention further comprise a triol component, including glycerol and derivatives thereof. As mentioned herein, we have found that glycerol surprisingly increases the chemical stability of compositions of the invention when compared similar compositions such as those disclosed in international patent application WO 87/04617, U.S. Pat. No. 5,525,635 and European Patent No. EP 292 495 B1.

Compositions of the invention are more chemically stable, for example, at higher temperatures and may therefore be more readily stored in warmer climates.

By "chemical stability", we include that the compositions of the invention may be stored under normal storage conditions, with an insignificant degree of chemical degradation or decomposition. Examples of "normal storage conditions" include temperatures of between minus 80 and plus 50° C. (preferably between 0 and 40° C. and more preferably ambient temperature, such as between 15 and 30° C.), pressures of between 0.1 and 2 bars (preferably atmospheric pressure), relative humidities of between 5 and 95% (preferably 10 to 60%), and/or exposure to 460 lux of UV/visible light, for prolonged periods (i.e. greater than or equal to six months). Under such conditions, compositions of the invention may be found to be less than about 15%, more preferably less than about 10%, and especially less than about 5%, chemically degraded/decomposed, or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

In particular, the chemical stability of the urea-based component is improved by the presence of the triol component.

According to a further aspect of the invention, there is provided a method of improving the storage stability of a pharmaceutical composition suitable for topical application to the nails and/or, particularly, the skin (and particularly the chemical stability of a urea-based component in such a composition) comprising:
(a) said urea-based component; as well as
(b) a diol component;
(c) an organic acid component; and
(d) optionally, an aqueous base,
which method comprises adding between about 4.5% (e.g. about 5%) and about 12% by weight based upon the total weight of the composition of a triol component to that composition prior to said storage.

Typical total amounts of triol, such as glycerol and/or derivatives, that may be employed in a composition of the invention may be in the range of about 4.5% to about 25%, such as about 4.75% to about 15%, for example about 5% (e.g. about 6%) to about 12% (e.g. about 10%), by weight based upon the total weight of the composition.

Compositions of the invention optionally comprise a volatile organic solvent. See for example international patent application WO 2011/019317. If employed, volatile organic solvent may be chosen so that it evaporates within about 5 minutes, more preferably within about 3 minutes after application in room temperature. A volatile organic solvent with a vapor pressure of at least 2 kPa at 20° C. may be used, for example polar solvents such as esters, alcohols, ketones and saturated hydrocarbons with a high vapor pressure (greater than about 2 kPa at 20° C.). Examples of suitable volatile organic solvents include methyl acetate, isopropanol (isopropyl alcohol), ethanol, acetone, methyl ethyl ketone and methyl isobutyl ketone, particularly ethyl acetate and/or butyl acetate.

Compositions of the invention optionally comprise an antifungal drug compound, such as one of the type mentioned hereinbefore. Examples of such compounds thus include imidazoles, such as miconazole, ketoconazole, econazole, bifonazole, butoconazole, fenticonazole, isoconazole, oxiconazole, sertaconazole, sulconazole, and tioconazole; triazoles, such as fluconazole, itraconazole, isavuconazole, ravuconazole, posaconazole, voriconazole, and terconazole; thiazoles, such as abafungin; echinocandins, such as anidulafungin, caspofungin, and micafungin; more preferably, allylamines, such as amorolfine, butenafine, particularly naftifine and, especially, terbinafine; and mixtures thereof.

If present, the antifungal drug compounds will be presented in a pharmaceutically effective amount, which amount may vary depending upon the particular antifungal component(s) selected, but may be in the range of about 0.01% to about 15% (e.g. about 10%), more preferably from about 0.2% to about 5%, more preferably from about 0.75% to about 2.5%, more preferably from about 0.8% to about 1.2%, by weight based on the total weight of the composition.

If the antifungal drug compounds are presented in compositions of the invention, the skilled person will appreciate that it may be necessary to correspondingly reduce the above-stated preferred concentration ranges of other active components, such as urea-based components and diol components (or organic acid components).

The urea-based compound may act in part as a keratolytic agent. Compositions of the invention optionally comprise a further keratolytic agents include sulphur-containing amino acids, such as cysteine, methionine, N-acetyl cysteine, homocysteine, methyl cysteine, ethyl cysteine, N-carbomyl cysteine, glutathione, cysteamine and derivatives thereof.

Furthermore, compositions of the invention may include compounds that improve texture during administration and on the nail during treatment. This results in an increased viscosity at administration which facilitates dosing. It also allows the product to stay at the surface of the nail to perform its effect. Preferably, according to one embodiment of the invention, the composition comprises a polymer having suitable viscosity-increasing properties (hereinafter referred to as a "viscosity-increasing agent"). Non-limiting examples of such compounds includes cellulose derivatives such as ethyl cellulose, cellulose acetate butyrate and polymethacrylates such as Eudragit. Suitable concentrations of such viscosity-increasing agents may be determined by a person skilled in the art.

If desired, the composition may further comprise a sequestering agent. Non-limiting examples of such sequestering agents include one or more of aminoacetic acids, phosphonates, phosphonic acids and mixtures of these. Sequestering agents can be metal complexing agents and thus, may form a complex with metals such as the alkali metals or alkaline earth metals. A preferred aminoacetic acid is ethylenediaminetetraacetic acid (EDTA). When included in the compositions, examples of suitable amounts of the sequestering agent include from about 0.01 to about 5% by weight, preferably from about 0.03% to about 0.5%.

Compositions of the invention may further comprises a detergent. Non-limiting examples of suitable detergents include Tween 80. Suitable concentrations of detergent are in the range of about 0.1% to about 5%, more preferably from about 0.5% to about 3%, even more preferably from about 0.7% to about 1.5%.

Other pharmaceutically acceptable carriers and excipients, such as stabilizers, penetration enhancers, and colouring agents may also be added to compositions of the invention as desired.

A preferred embodiment of the invention comprises about 50% to about 70% of a diol component, such as propylene glycol, about 5 (e.g. about 7%) to about 15% (e.g. about 12%) of an organic acid component, such as lactic acid, about 8% (e.g. about 15%) to about 25% of a urea-based component, such as urea and/or carbamide peroxide, about 5% to about 10% (e.g. about 7.5%) of a triol component, such as glycerol, and, optionally, about 2% to about 5% of aqueous base, such as 10M sodium hydroxide.

Compositions of the invention may be prepared by standard techniques, and using standard equipment, known to the skilled person. Other ingredients may be incorporated by standard mixing or other formulation principles.

Compositions of the invention may thus be incorporated into various kinds of pharmaceutical preparations intended for topical administration using standard techniques (see, for example, Lachman et al, "*The Theory and Practice of Industrial Pharmacy*", Lea & Febiger, 3$^{rd}$ edition (1986) and "*Remington: The Science and Practice of Pharmacy*", Gennaro (ed.), Philadelphia College of Pharmacy & Sciences, 19$^{th}$ edition (1995)), by combining compositions of the invention with conventional pharmaceutical additives and/or excipients used in the art for such preparations.

Compositions of the invention are preferably administered directly to the skin and/or nail. For instance, the composition is administered on and around a human toenail or fingernail affected by a fungal disease, such as onychomycosis. This may be performed by covering each affected nail with a liquid/solution composition from about twice or three times per day to about once per week with a layer of the composition. The composition may also be applied to the edge of a nail. Administration of such a composition may be achieved by means of a suitable device such as a drop tip, a small brush or a spatula.

Compositions of the invention demonstrate high penetration of e.g. the nail. This can be assessed by an in vitro method for nail penetration. For example, a Franz cell can be used to study the penetration through a membrane from a bovine hoof as described in the examples below.

Accordingly, compositions of the invention may be employed in the treatment of nail diseases, such as fungal infections of the nail, for example onychomycosis.

According to a further aspect of the invention there is provided a method for treating a nail disease which comprises administering a composition of the invention to the nail of a patient.

In accordance with the invention, compositions of the invention may be combined in treatment with one or more other antifungal nail treatments, including laser therapy, oral antifungal preparations, such as terbinafine and/or topical antifungal treatments, such as preparations comprising ciclopiroxolamine, amorolfine and the like.

By "treatment" of nail and/or skin diseases we include the therapeutic and/or cosmetic treatment, as well as the symptomatic, prophylactic and palliative treatment of the disease. Treatment thus includes the alleviation of symptoms of fungal diseases as well as the improvement in the appearance of nails and/or skin.

Compositions of the invention are easy and inexpensive to manufacture, are easily applied topically, and may enable rapid relief of symptoms, such as those described hereinbefore.

Compositions of the invention may also have the advantage that they may be prepared using established pharmaceutical processing methods and employ materials that are approved for use in food, pharmaceuticals or cosmetics and/or of like regulatory status.

Compositions of the invention may also have the advantage that they may be more efficacious than, be less toxic than, be longer acting than, be more potent than, produce fewer side effects than, be more easily absorbed than, possess a better patient acceptability than, have a better pharmaceutical profile than, and/or have other useful pharmacological, physical, or chemical properties over, pharmaceutical compositions known in the prior art, whether for use in the treatment of skin or nail diseases or otherwise.

The invention is illustrated by way of the following examples, with reference to the attached FIG. 1, which shows a comparison of chemical stability of compositions of the invention compared to a commercial composition of the prior art.

EXEMPLIFICATION

Comparative Example 1

Marketed Formulation

A composition with ingredients in the following proportions was prepared in a three batch sizes (450 kg, 150 kg and 20 kg), each by dissolving urea in propylene glycol before adding lactic acid and then 10M aqueous NaOH.

| Component | w/w % |
|---|---|
| Propylene glycol | 66.4 |
| Urea | 20 |
| Lactic acid | 10 |
| 10M NaOH (aq.) | 3.6 |

Example 2

Composition Including Glycerol I

A composition with ingredients in the following proportions was prepared in a batch size of 0.5 kg by dissolving urea in propylene glycol and glycerol before adding lactic acid and then 10M aqueous NaOH.

| Component | w/w % |
|---|---|
| Propylene glycol | 59.76 |
| Glycerol | 6.64 |
| Urea | 20 |
| Lactic acid | 10 |
| 10M NaOH (aq.) | 3.6 |

Example 3

Composition Including Glycerol II

A composition with ingredients in the following proportions was prepared in a batch size of 50 g by dissolving urea hydrogen peroxide in lactic acid and glycerol before adding propylene glycol and urea. 10M NaOH was added at the end of the sample preparation when the urea was fully dissolved.

| Component | w/w % |
|---|---|
| Propylene glycol | 56.76 |
| Glycerol | 6.64 |
| Urea | 17 |
| Urea hydrogen peroxide | 6 |
| Lactic acid | 10 |
| 10M NaOH (aq.) | 3.6 |

Example 4

Composition Including Glycerol III

A composition with ingredients in the following proportions was prepared in a batch size of 3 kg by dissolving urea in propylene glycol and glycerol before adding lactic acid and then 10M aqueous NaOH.

| Component | w/w % |
|---|---|
| Propylene glycol | 56.4 |
| Glycerol | 10 |
| Urea | 20 |
| Lactic acid | 10 |
| 10M NaOH (aq.) | 3.6 |

Example 5

Composition Including Glycerol IV

A composition with ingredients in the following proportions was prepared in a batch size of 5 kg by dissolving urea hydrogen peroxide in lactic acid and glycerol before adding propylene glycol and urea. 10M NaOH was added at the end of the sample preparation when the urea was fully dissolved.

| Component | w/w % |
|---|---|
| Propylene glycol | 53.90 |
| Glycerol | 10 |
| Urea | 17.5 |
| Urea hydrogen peroxide | 5 |
| Lactic acid | 10 |
| 10M NaOH (aq.) | 3.6 |

Example 6

Composition Including Glycerol V

A composition with ingredients in the following proportions was prepared in in accordance with the procedure described in Example 2 in a batch size of 0.2 kg.

| Component | w/w % |
|---|---|
| Propylene glycol | 61.4 |
| Glycerol | 5 |
| Urea | 20 |
| Lactic acid | 10 |
| 10M NaOH (aq.) | 3.6 |

Example 7

Comparative Test

Chemical decomposition of urea in the three different product batches (as described in Comparative Example 1) was studied in three different stability studies and compared to those of Examples 2 and 6. An analytical method (RP-HPLC-UV) was used for determination of urea content.

The results are shown in Table 1 below and in FIG. 1. All three Example 1 batches are out of specification (OOS; more than 10% degradation) at 6 months. One is OOS at 3 months. However, the urea content for Example 2 is within specification for the whole of the 6 month study, and that for Example 6 is within specification after 3 months.

Thus, glycerol improves the stability of urea in a product formulation stored at accelerated conditions (40° C.).

TABLE 1

Urea stability with and without glycerol for 6 months at 40° C.

| Formulations | Months | | | | | |
|---|---|---|---|---|---|---|
| | 0 | 1 | 1.5 | 2 | 3 | 6 |
| Example 1 (450 kg batch) | 20.10 | 19.50 | — | 18.80 | 18.30 | *17.20* |
| Example 1 (150 kg batch) | 20.00 | 19.20 | — | 18.20 | 18.10 | *16.40* |
| Example 1 (20 kg batch) | 20.00 | 18.60 | — | 18.90 | *17.80* | *16.90* |
| Example 2 | 20.16 | — | 19.22 | — | 18.44 | 18.31 |
| Example 6 | 20.06 | — | — | — | 18.92 | — |

The italicised values are OOS.

The invention claimed is:

1. A pharmaceutical composition in the form of a liquid or solution, which comprises:
    (a) about 3% to about 30% by weight based upon the total weight of the composition of urea and/or urea peroxide;
    (b) about 40% to about 80% by weight based upon the total weight of the composition of one or more of the group selected from ethylene glycol, propylene glycol, butanediol, pentanediol, hexanediol and mixtures thereof;
    (c) about 2% to about 15% by weight based upon the total weight of the composition of one or more of the group a hydroxybutyric acid, a hydroxypropionic acid, glycolic acid, citric acid, malic acid and tartaric acid;
    (d) about 5% to about 12% by weight based upon the total weight of the composition of glycerol; and
    (e) an amount of aqueous base sufficient to provide a final pH of the composition in the range of about 2 to about 6.

2. The pharmaceutical composition of claim 1, which comprises:
    (a) about 3% to about 30% by weight based upon the total weight of the composition of urea;
    (b) about 40% to about 80% by weight based upon the total weight of the composition of propylene glycol;
    (c) about 2% to about 15% by weight based upon the total weight of the composition of lactic acid;
    (d) about 5% to about 12% by weight based upon the total weight of the composition of glycerol; and
    (e) an amount of aqueous sodium hydroxide sufficient to provide a final pH of the composition in the range of about 3 to about 5.

3. The pharmaceutical composition of claim 1, which further comprises about 0.01% to about 5% by weight based upon the total weight of the composition of ethylenediaminetetraacetic acid.

4. The pharmaceutical composition of claim 2, which further comprises about 0.01% to about 5% by weight based upon the total weight of the composition of ethylenediaminetetraacetic acid.

5. A pharmaceutical composition in the form of a liquid or solution, which comprises:
    (a) about 5% to about 25% by weight based upon the total weight of the composition of urea and/or urea peroxide;
    (b) about 45% to about 75% by weight based upon the total weight of the composition of one or more of the group selected from ethylene glycol, propylene glycol, butanediol, pentanediol, hexanediol and mixtures thereof;
    (c) about 3% to about 15% by weight based upon the total weight of the composition of one or more of the group a hydroxybutyric acid, a hydroxypropionic acid, glycolic acid, citric acid, malic acid and tartaric acid;

(d) about 5% to about 12% by weight based upon the total weight of the composition of glycerol; and (e) an amount of aqueous base sufficient to provide a final pH of the composition in the range of about 2 to about 6.

6. The pharmaceutical composition of claim 5, which comprises:
(a) about 5% to about 25% by weight based upon the total weight of the composition of urea;
(b) about 45% to about 75% by weight based upon the total weight of the composition of propylene glycol;
(c) about 3% to about 15% by weight based upon the total weight of the composition of lactic acid;
(d) about 5% to about 12% by weight based upon the total weight of the composition of glycerol; and
(e) an amount of aqueous sodium hydroxide sufficient to provide a final pH of the composition in the range of about 3 to about 5.

7. The pharmaceutical composition of claim 5, which further comprises 0.03% to about 0.5% by weight based upon the total weight of the composition of ethylenediaminetetraacetic acid.

8. The pharmaceutical composition of claim 6, which further comprises 0.03% to about 0.5% by weight based upon the total weight of the composition of ethylenediaminetetraacetic acid.

9. A pharmaceutical composition in the form of a liquid or solution, which comprises:
(a) about 8% to about 25% by weight based upon the total weight of the composition of urea and/or urea peroxide;
(b) about 50% to about 75% by weight based upon the total weight of the composition of one or more of the group selected from ethylene glycol, propylene glycol, butanediol, pentanediol, hexanediol and mixtures thereof;
(c) about 4% to about 12% by weight based upon the total weight of the composition of one or more of the group a hydroxybutyric acid, a hydroxypropionic acid, glycolic acid, citric acid, malic acid and tartaric acid;
(d) about 5% to about 10% by weight based upon the total weight of the composition of glycerol; and
(e) an amount of aqueous base sufficient to provide a final pH of the composition in the range of about 2 to about 6.

10. The pharmaceutical composition of claim 9, which comprises:
(a) about 8% to about 25% by weight based upon the total weight of the composition of urea;
(b) about 50% to about 75% by weight based upon the total weight of the composition of propylene glycol;
(c) about 4% to about 12% by weight based upon the total weight of the composition of lactic acid;
(d) about 5% to about 10% by weight based upon the total weight of the composition of glycerol; and
(e) an amount of aqueous sodium hydroxide sufficient to provide a final pH of the composition in the range of about 3 to about 5.

11. The pharmaceutical composition of claim 9 which further comprises 0.03% to about 0.5% by weight based upon the total weight of the composition of ethylenediaminetetraacetic acid.

12. The pharmaceutical composition of claim 10 which further comprises 0.03% to about 0.5% by weight based upon the total weight of the composition of ethylenediaminetetraacetic acid.

13. A method of treatment of a fungal infection of the nail, which method comprises administration of a pharmaceutical composition of claim 1 to a person suffering from, or susceptible to, that disease.

14. A method of treatment of a fungal infection of the nail, which method comprises administration of a pharmaceutical composition of claim 2 to a person suffering from, or susceptible to, that disease.

15. A method of treatment of a fungal infection of the nail, which method comprises administration of a pharmaceutical composition of claim 3 to a person suffering from, or susceptible to, that disease.

16. A method of treatment of a fungal infection of the nail, which method comprises administration of a pharmaceutical composition of claim 4 to a person suffering from, or susceptible to, that disease.

17. A method of treatment of a fungal infection of the nail, which method comprises administration of a pharmaceutical composition of claim 5 to a person suffering from, or susceptible to, that disease.

18. A method of treatment of a fungal infection of the nail, which method comprises administration of a pharmaceutical composition of claim 6 to a person suffering from, or susceptible to, that disease.

19. A method of treatment of a fungal infection of the nail, which method comprises administration of a pharmaceutical composition of claim 7 to a person suffering from, or susceptible to, that disease.

20. A method of treatment of a fungal infection of the nail, which method comprises administration of a pharmaceutical composition of claim 8 to a person suffering from, or susceptible to, that disease.

21. A method of treatment of a fungal infection of the nail, which method comprises administration of a pharmaceutical composition of claim 9 to a person suffering from, or susceptible to, that disease.

22. A method of treatment of a fungal infection of the nail, which method comprises administration of a pharmaceutical composition of claim 10 to a person suffering from, or susceptible to, that disease.

23. A method of treatment of a fungal infection of the nail, which method comprises administration of a pharmaceutical composition of claim 11 to a person suffering from, or susceptible to, that disease.

24. A method of treatment of a fungal infection of the nail, which method comprises administration of a pharmaceutical composition of claim 12 to a person suffering from, or susceptible to, that disease.

25. A method of treatment of onychomycosis, which method comprises administration of a pharmaceutical composition of claim 1 to a person suffering from, or susceptible to, that disease, wherein the treatment comprises applying the composition in the form of a liquid or solution to an affected nail.

26. A method of treatment of onychomycosis, which method comprises administration of a pharmaceutical composition of claim 2 to a person suffering from, or susceptible to, that disease, wherein the treatment comprises applying the composition in the form of a liquid or solution to an affected nail.

27. A method of treatment of onychomycosis, which method comprises administration of a pharmaceutical composition of claim 3 to a person suffering from, or susceptible to, that disease, wherein the treatment comprises applying the composition in the form of a liquid or solution to an affected nail.

28. A method of treatment of onychomycosis, which method comprises administration of a pharmaceutical composition of claim 4 to a person suffering from, or susceptible to, that disease, wherein the treatment comprises applying the composition in the form of a liquid or solution to an affected nail.

29. A method of treatment of onychomycosis, which method comprises administration of a pharmaceutical composition of claim 5 to a person suffering from, or susceptible to, that disease, wherein the treatment comprises applying the composition in the form of a liquid or solution to an affected nail.

30. A method of treatment of onychomycosis, which method comprises administration of a pharmaceutical composition of claim 6 to a person suffering from, or susceptible to, that disease, wherein the treatment comprises applying the composition in the form of a liquid or solution to an affected nail.

31. A method of treatment of onychomycosis, which method comprises administration of a pharmaceutical composition of claim 7 to a person suffering from, or susceptible to, that disease, wherein the treatment comprises applying the composition in the form of a liquid or solution to an affected nail.

32. A method of treatment of onychomycosis, which method comprises administration of a pharmaceutical composition of claim 8 to a person suffering from, or susceptible to, that disease, wherein the treatment comprises applying the composition in the form of a liquid or solution to an affected nail.

33. A method of treatment of onychomycosis, which method comprises administration of a pharmaceutical composition of claim 9 to a person suffering from, or susceptible to, that disease, wherein the treatment comprises applying the composition in the form of a liquid or solution to an affected nail.

34. A method of treatment of onychomycosis, which method comprises administration of a pharmaceutical composition of claim 10 to a person suffering from, or susceptible to, that disease, wherein the treatment comprises applying the composition in the form of a liquid or solution to an affected nail.

35. A method of treatment of onychomycosis, which method comprises administration of a pharmaceutical composition of claim 11 to a person suffering from, or susceptible to, that disease, wherein the treatment comprises applying the composition in the form of a liquid or solution to an affected nail.

36. A method of treatment of onychomycosis, which method comprises administration of a pharmaceutical composition of claim 12 to a person suffering from, or susceptible to, that disease, wherein the treatment comprises applying the composition in the form of a liquid or solution to an affected nail.

* * * * *